(12) United States Patent
Mitra (10) Patent No.: US 9,897,556 B2
(45) Date of Patent: Feb. 20, 2018

(54) ELEMENTAL ANALYSIS USING TEMPORAL GATING OF A PULSED NEUTRON GENERATOR

(71) Applicant: Sandia Corporation, Albuquerque, NM (US)

(72) Inventor: Sudeep Mitra, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 73 days.

(21) Appl. No.: 14/688,117

(22) Filed: Apr. 16, 2015

(65) Prior Publication Data

US 2015/0323473 A1 Nov. 12, 2015

Related U.S. Application Data

(60) Provisional application No. 61/990,331, filed on May 8, 2014.

(51) Int. Cl.
 *G01N 23/02* (2006.01)
 *G01T 3/00* (2006.01)
 *G01V 5/00* (2006.01)

(52) U.S. Cl.
 CPC .......... *G01N 23/02* (2013.01); *G01N 23/025* (2013.01); *G01T 3/00* (2013.01); *G01V 5/0091* (2013.01)

(58) Field of Classification Search
 CPC ...... G01N 23/02; G01N 23/025; G01T 3/005; G01V 5/0091
 See application file for complete search history.

(56) References Cited

U.S. PATENT DOCUMENTS

| 5,200,626 | A | 4/1993 | Schultz et al. |
| 5,825,290 | A | 10/1998 | Lian et al. |
| 7,359,480 | B2 | 4/2008 | Slaughter et al. |
| 7,430,479 | B1 * | 9/2008 | Holslin .................. G01T 1/167 250/359.1 |
| 8,304,740 | B1 * | 11/2012 | Frank .................. G01V 5/0075 250/370.11 |
| 8,384,004 | B1 * | 2/2013 | Rowland .................. G01T 3/00 250/207 |

(Continued)

OTHER PUBLICATIONS

Tan, et al., "A Multiple Time-Gated System for Pulsed Digital Gamma-Ray Spectroscopy", Journal of Radioanalytical and Nuclear Chemistry, vol. 276, No. 3 (2008), pp. 639-643.

*Primary Examiner* — Christine Sung
(74) *Attorney, Agent, or Firm* — Medley, Behrens & Lewis LLC; Samantha Updegraff (57) ABSTRACT

Technologies related to determining elemental composition of a sample that comprises fissile material are described herein. In a general embodiment, a pulsed neutron generator periodically emits bursts of neutrons, and is synchronized with an analyzer circuit. The bursts of neutrons are used to interrogate the sample, and the sample outputs gamma rays based upon the neutrons impacting the sample. A detector outputs pulses based upon the gamma rays impinging upon the material of the detector, and the analyzer circuit assigns the pulses to temporally-based bins based upon the analyzer circuit being synchronized with the pulsed neutron generator. A computing device outputs data that is indicative of elemental composition of the sample based upon the binned pulses.

20 Claims, 9 Drawing Sheets

(56) References Cited

U.S. PATENT DOCUMENTS

| | | | | |
|---|---|---|---|---|
| 2001/0046274 A1* | 11/2001 | Craig | ............... | G01T 1/295 |
| | | | | 376/154 |
| 2002/0036260 A1* | 3/2002 | Adolph | ............... | G01V 5/104 |
| | | | | 250/269.1 |
| 2005/0028586 A1* | 2/2005 | Smits | ............... | G01V 5/12 |
| | | | | 73/152.14 |
| 2010/0046690 A1* | 2/2010 | Proctor | ............... | G01V 5/0091 |
| | | | | 376/154 |
| 2010/0224786 A1* | 9/2010 | Gullickson | ............... | G01T 1/167 |
| | | | | 250/370.03 |
| 2011/0176648 A1 | 7/2011 | Rowland et al. | | |
| 2012/0046867 A1* | 2/2012 | Faber | ............... | G01T 1/1611 |
| | | | | 702/8 |
| 2012/0116730 A1* | 5/2012 | Prasad | ............... | G01T 3/00 |
| | | | | 703/2 |
| 2012/0213319 A1 | 8/2012 | Kwan et al. | | |
| 2012/0286164 A1 | 11/2012 | Piefer | | |
| 2013/0276639 A1 | 10/2013 | Chen | | |
| 2014/0197307 A1* | 7/2014 | Jorion | ............... | G01T 1/17 |
| | | | | 250/252.1 |
| 2015/0090871 A1* | 4/2015 | Chace | ............... | E21B 47/0005 |
| | | | | 250/269.7 |
| 2016/0194558 A1* | 7/2016 | Riddle | ............... | G01T 1/16 |
| | | | | 250/390.11 |

* cited by examiner

ELEMENTAL ANALYSIS USING TEMPORAL GATING OF A PULSED NEUTRON GENERATOR

RELATED APPLICATION

This application claims priority to U.S. Provisional Patent Application No. 61/990,331, filed on May 8, 2014, and entitled "ELEMENTAL ANALYSES USING TEMPORAL GATING OF A PULSED NEUTRON GENERATOR", the entirety of which is incorporated herein by reference.

STATEMENT OF GOVERNMENTAL INTEREST

This invention was developed under contract DE-AC04-94AL85000 between Sandia Corporation and the U.S. Department of Energy. The U.S. Government has certain rights in this invention.

BACKGROUND

Conventional techniques for obtaining information regarding elemental composition of a sample that includes fissile material are time consuming and require a laboratory environment. With more particularity, an exemplary conventional technique requires that a sample be dissolved in a solvent, and subsequently the dissolved sample is analyzed to acquire information about the elemental composition thereof. Further, conventional techniques that use active neutron interrogation to acquire information about elemental composition of samples that comprise non-fissile materials are not readily adaptable for use in obtaining information about elemental composition of samples that include fissile materials. This is because when a sample that includes fissile material is actively interrogated with neutrons, delayed gamma rays are produced, causing difficulties in isolating inelastic pre-fission gamma rays.

SUMMARY

Various technologies relating to in situ and real-time obtainment of information that is indicative of elemental composition of a sample that comprises fissile material (e.g., one or more actinides) are described herein. In a general embodiment, the present disclosure provides a system that is configured to obtain such information includes a pulsed neutron generator and a detector. A sample that comprises fissile material is placed in between the neutron generator and the detector. The system also includes an analyzer circuit that is in communication with and synchronized with the pulsed neutron generator. With more particularity, the analyzer circuit comprises a clock, which is initialized and started at the onset of each pulse of neutrons emitted by the neutron generator. Further, the analyzer circuit defines a plurality of bins, where each of the bins corresponds to a respective (non-overlapping) time window per cycle of the pulsed neutron generator.

In an example, the pulsed neutron generator can be configured to generate pulses of neutrons at a pulse rate of 10 kHz. Further, the pulsed neutron generator may have a duty cycle of about 25%. Thus, the pulsed neutron generator emits a pulse of neutrons for 25 µs, followed by 75 µs where the pulsed neutron generator does not emit neutrons. As mentioned previously, the analyzer circuit can define a plurality of bins that respectively correspond to the cycle period of the pulsed neutron generator. In a non-limiting example, the analyzer circuit can define 10 bins for the cycle, where the first five bins each correspond to a 5 µs time window (corresponding to the 25 µs "on" period) and the last five bins each correspond to a 15 µs time window (corresponding to the 75 µs "off" period). The system also includes a computing apparatus that is in communication with the analyzer circuit, where the computing apparatus is configured to output data that is indicative of elemental composition of the sample based upon data assigned to the bins.

In operation, the pulsed neutron generator is activated, causing fast neutrons to be periodically and isotropically emitted therefrom. At least some of these fast neutrons will enter the sample. The neutrons that enter the sample cause nuclear reactions to occur, wherein such reactions cause gamma rays to be emitted from the sample. The gamma rays include: 1) gamma rays produced from inelastic neutron scattering reactions; 2) gamma rays produced from thermal neutron capture reactions; 3) prompt fission gamma rays; and 4) β-delayed gamma rays. At least some of the gamma rays impinge upon the detector material (which may be a scintillating material or solid state material, such as germanium), and the detector outputs signals based upon the gamma rays that impinge upon the material, wherein the signals are indicative of energies of the gamma rays.

The analyzer circuit receives the signals output by the detector, which include pulses that are indicative of energies of gamma rays impinging upon the material of the detector. The analyzer circuit assigns the pulses to bins based upon when the leading edges of the pulses occur relative to when the pulsed neutron generator commenced emitting a most recent pulse of neutrons. Continuing with the example set forth above, all pulses received by the analyzer circuit in the first 5 µs after the pulsed neutron generator commenced emitting a pulse of neutrons are placed in a first bin, pulses (pulse amplitudes) received by the analyzer circuit between 6 and 10 µs after the pulsed neutron generator commenced a pulse of neutrons are placed in the second bin, and so forth.

After the pulsed neutron generator has emitted several pulses of neutrons, the computing device can analyze the time-resolved pulses output by the detector and can generate and output an indication of elemental composition of the sample. With more particularity, delayed gamma rays are identified based upon the time-resolved pulses, allowing for acquisition of information pertaining to the gamma rays produced based upon inelastic neutron scattering reactions and information pertaining to thermal neutron capture reactions, which are indicative of identities of elements that produce such gamma rays. In other words, "noise" corresponding to the delayed gamma rays can be extrapolated from the pulses, leaving data that is indicative of elemental composition of the sample. As noted above, information that is indicative of elemental composition of the sample can be output in situ and in real-time, wherein real-time, in an example, means within two hundred micro-seconds of the pulsed neutron generator being initiated. In another example, real-time means within thirty seconds of the pulsed neutron generator being initiated. In yet another example, real-time means within thirty minutes of the pulsed neutron generator being initiated. Accordingly, the features described herein allow for in situ and real-time obtainment of information about elemental composition of samples that include fissile materials in a variety of applications, such as airport screening, cargo screening, and in general applications from oil well logging to the cement industry and the like.

Additional features and advantages are described herein, and will be apparent from the following Detailed Description and the figures.

DETAILED DESCRIPTION

Figure 1:
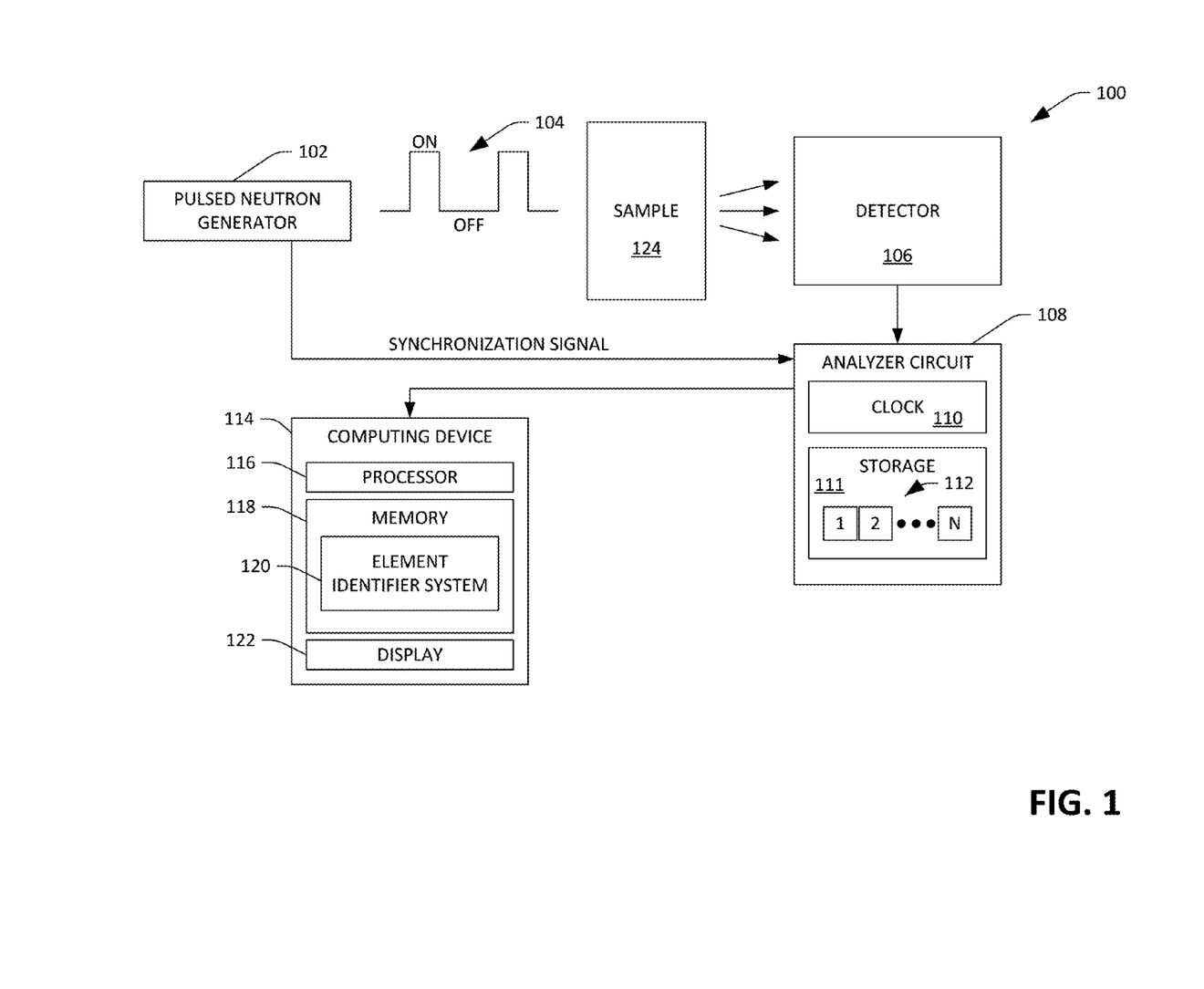
FIG. 1 is a functional block diagram of an exemplary system that is configured to output data that is indicative of elemental composition of a sample that comprises fissile material.

Various technologies pertaining to obtaining, in situ and in real-time, information that is indicative of elemental composition of a sample that comprises fissile material (e.g., an actinide) are disclosed herein. With reference now to FIG. 1, an exemplary system 100 that is configured to generate data that is indicative of elemental composition of a sample that comprises fissile material is illustrated. The system 100 includes a pulsed neutron generator 102. In an example, the pulsed neutron generator 102 can be a deuterium-deuterium (D-D) neutron generator. In another example, the pulsed neutron generator 102 can be a deuterium-tritium (D-T) neutron generator. The pulsed neutron generator 102 is configured to periodically emit bursts of neutrons. In an exemplary embodiment, the pulsed neutron generator 102 can be configured to isotropically emit pulses of neutrons at a rate of about 10 kHz. Further, the pulsed neutron generator 102 can have a duty cycle of about 25%. Operation of the pulsed neutron generator 102 is illustrated by square wave 104, where the pulsed neutron generator 102 emits neutrons during an "on" state, and charges (and fails to emit neutrons) during an "off" state.

The system 100 further comprises a detector 106 is configured to emit signals based upon gamma rays impinging upon material of the detector 106. In an example, the material of the detector 106 may be germanium, although other materials are contemplated. The detector 106 further comprises a readout integrated circuit (ROIC) (not shown) that is configured to output electric signals at a suitable sampling rate, where amplitude of the electric signals is based upon energies of gamma rays impinging upon the detector 106. While the system 100 is illustrated as including a single detector, it is to be understood that the system 100 can include numerous detectors. For example, the system 100 can include eight detectors, sixteen detectors, etc.

The system 100 also includes an analyzer circuit 108 that is in communication with the ROIC of the detector 106, as well as with the pulsed neutron generator 102. With more particularity, the analyzer circuit 108 is synchronized with the pulsed neutron generator 102. The analyzer circuit 108 comprises a clock 110 that is synchronized with the pulsing of the pulsed neutron generator 102. That is, the pulsed neutron generator 102 is configured to emit a synchronization signal, where the synchronization signal is indicative of when the "on" state is to commence. The clock 110 of the analyzer circuit 108 is initialized and started based upon the synchronization signal output by the pulsed neutron generator 102.

The analyzer circuit 108 includes computer-readable storage 111, which comprises a plurality of bins (also referred to as gates) 112, where each of the bins 112 correspond to a respective time window in a cycle of the pulsed neutron generator 102. In a non-limiting example, the analyzer circuit 108 can define 10 bins, and a period of a cycle of the pulsed neutron generator 102 can be 100 μs. Each of the 10 bins may correspond to a 10 μs time window in the period of the cycle. Thus, the commencement of the "on" state of the neutron generator occurs at time 0, a first bin in the plurality of bins 112 can correspond to the time window of 0-9 μs, a second bin can correspond to the time window of 10-19 μs, a third bin can correspond to the time window of 20-29 μs, and so on. While the above example indicates that each bin has a time window of a common duration corresponding thereto, it is to be understood that the bins may have different time durations corresponding thereto. For example, the first bin may correspond to a 5 μs time window, while the third bin may correspond to a 15 μs time window. An operator can define both a number of bins in the plurality of bins 112, as well as respective time windows that correspond to each bin in the plurality of bins 112.

The system 100 further includes a computing device 114 that is in communication with the analyzer circuit 108. For example, the computing device 114 can be in wired or wireless communication with the analyzer circuit 108. The computing device 114 comprises a processor 116 and a memory 118 that includes instructions that are executed by the processor 116. The memory 118 includes an element identifier system 120 that is configured to output data that is indicative of elemental composition of a sample that comprises fissile material. In an example, the computing device 114 can include a display 122, and the element identifier system 120, when executed by the processor 116, can be configured to output the data that is indicative of the elemental composition of the sample to the display 122. This data, for example, may be a plot that is indicative of elemental composition of a sample. The computing device 114 may be any suitable computing device, such as a desktop computing device, a laptop computing device, a tablet (slate) computing device, a mobile telephone, a spectrometer, or the like.

Operation of the system 100 is now set forth. A sample 124 is provided, where the sample includes fissile material. In an example, the sample 124 can be positioned between the pulsed neutron generator 102 and the detector 106. The pulsed neutron generator 102 is initiated, thereby causing the pulsed neutron generator 102 to emit pulses of neutrons as shown by the square wave 104. At least some of the neutrons emitted by the pulsed neutron generator 102 enter the sample 124, causing nuclear reactions to occur in the sample 124, which in turn causes gamma rays to be emitted from the sample 124. As will be described in greater detail below, gamma rays emitted from the sample 124 include gamma rays produced by inelastic neutron scattering (INS) reactions, gammas produced by thermal neutron capture (TNC) reactions, prompt fission gamma rays, and β-delayed gamma rays. Generally, the INS reactions occur concurrently in time with the neutron pulse, while the TNC reactions are delayed by the slowing down time of neutrons in the matrix of the sample 124. The prompt fission and β-delayed gamma rays will be collectively referred to herein as delayed gamma rays, and are observed at the detector 106 throughout the cycle of the pulsed neutron generator 102.

The above-referenced gamma rays impinge upon the material of the detector 106, and the ROIC of the detector 106 outputs electric signals based upon energies of the gamma rays that impinge upon the detector 106. With more particularity, when a gamma ray impinges upon the material of the detector 106, an electrical pulse is created that has an amplitude indicative of energy of the gamma ray. The ROIC reads out the electrical pulse, and the analyzer circuit 108 receives the electrical pulse.

As indicated previously, the analyzer circuit 108 is synchronized with the pulsed neutron generator 102, such that the clock 110 is initialized and started at the commencement of each burst of neutrons output by the neutron generator 102. The analyzer circuit 108 is configured to assign each pulse output by the detector 106 to one of the bins 112 in the storage 111 based upon a value of the clock 110 when the electrical pulse is received at the analyzer circuit 108. With more particularity, the analyzer circuit 108 can be configured to tag each incoming pulse from the detector 106 with the arrival time of the pulse relative to when the neutron burst emitted by the pulsed neutron generator 102 commenced (based upon a value of the clock 110). The pulse (e.g., the amplitude) may then be assigned to an appropriate bin based upon the time assigned to the pulse by the analyzer circuit 108.

The computing device 114 can be provided with the binned amplitudes by way of the wired or wireless connection between the analyzer circuit 108 and the computing device 114. The element identifier system 120, when executed by the processor 116 of the computing device 114, can output data (e.g., to the display 122) based upon the binned amplitude values of the pulsed output by the detector 106. Briefly, as the pulsed neutron generator 102 emits bursts of neutrons over time, delayed gamma rays will reach an equilibrium, and such equilibrium can be identified by analyzing amplitude values in bins that correspond to time windows that are later in the burst cycle (e.g., later in the "off" state) of the pulsed neutron generator 102. Once the equilibrium is identified, the equilibrium can be extrapolated from the captured data, leaving data that corresponds to gamma rays produced by INS and TNC reactions, which produce spectra that is characteristic of elemental composition of the sample 124. In other words, "noise" can be removed from the data using the time-resolved electric pulses. The element identifier system 120 can compare the above-referenced spectra with spectra observed from samples with known elemental compositions, and the element identifier system 120 can output the information that is indicative of the elemental composition of the sample 124 based upon such comparison.

Figure 2:
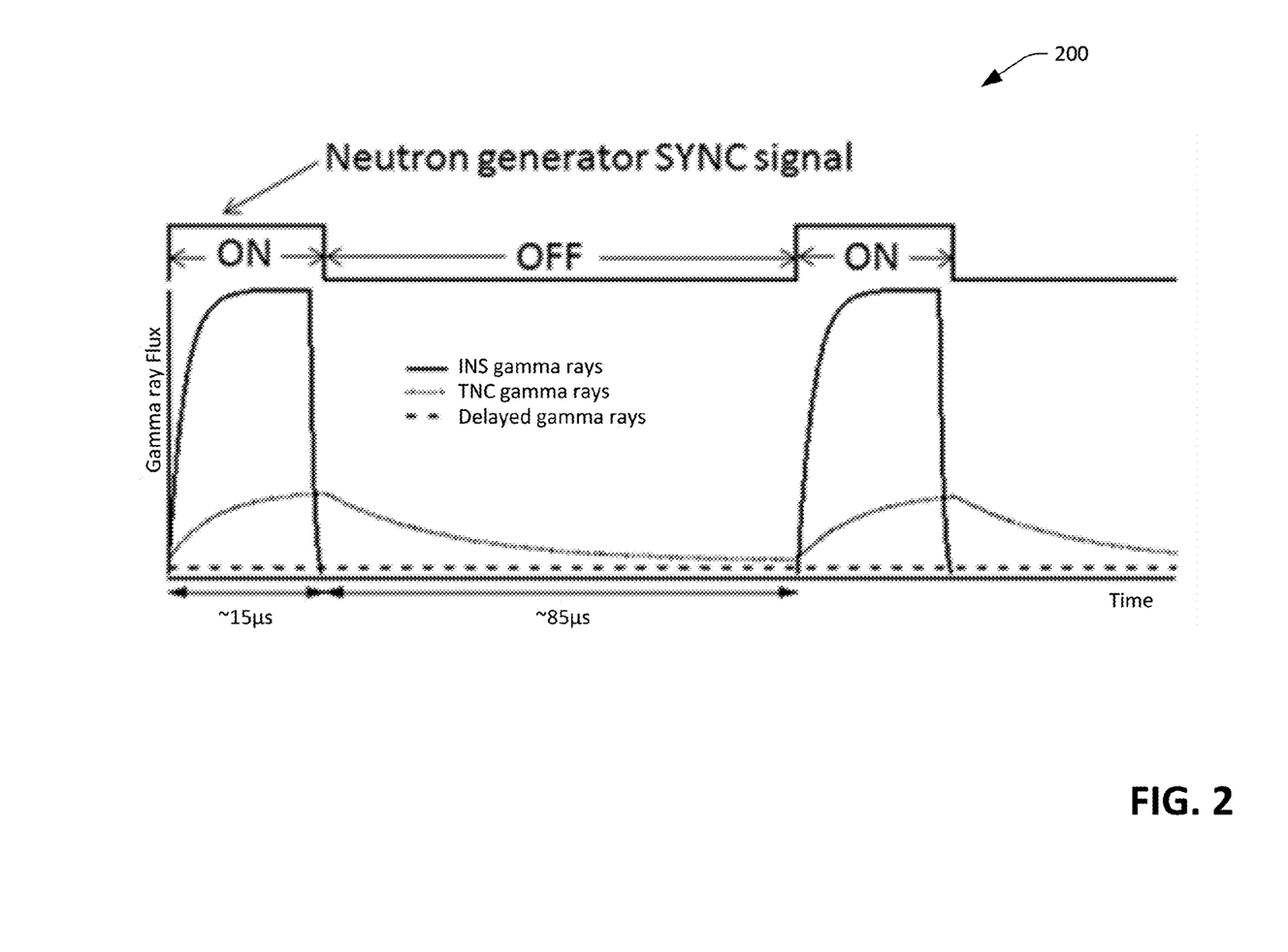
FIG. 2 is a plot that illustrates production of different types of gamma rays relative to "on" and "off" states of a pulsed neutron generator.

Now referring to FIG. 2, an exemplary plot 200 that illustrates when INS gamma rays, TNC gamma rays, and delayed gamma rays are detected at the detector 106 relative to "on" and "off" states of the pulsed neutron generator 102 is depicted. As shown in FIG. 2, the sample 124 emits INS gamma rays concurrently in time with the pulsed neutron generator 102 emitting a burst of neutrons. It can also be observed that TNC gamma rays are emitted from the sample 124 concurrently with the pulsed neutron generator 102 emitting a burst of neutrons, but also are observed during the "off" state of the pulsed neutron generator 102. Further, after several cycles, the delayed gamma rays reach an equilibrium. Once the equilibrium is identified (as indicated previously), the equilibrium can be taken into account to determine a spectra corresponding to the INS gamma rays and the TNC gamma rays.

Figure 3:
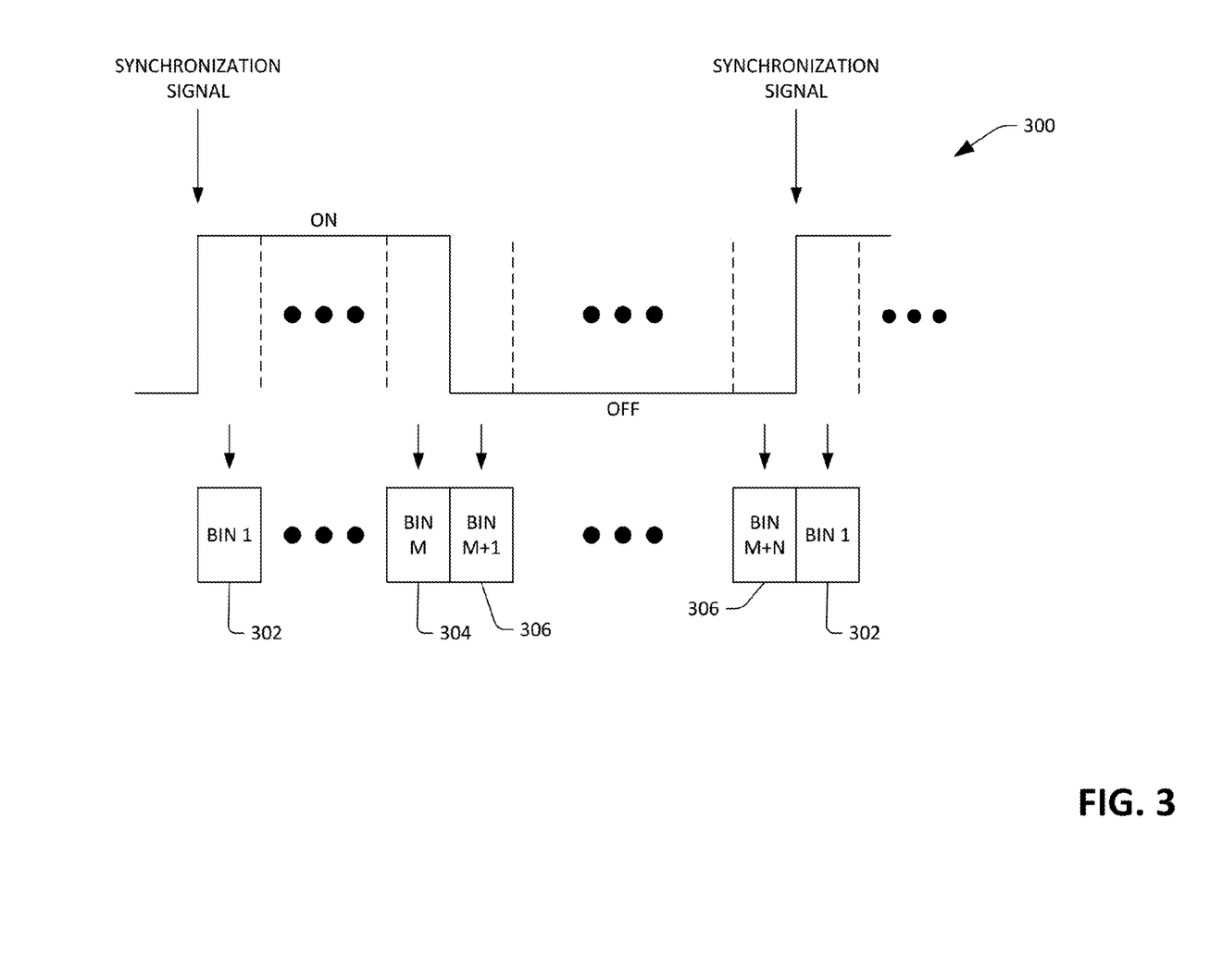
FIG. 3 illustrates bins corresponding to time windows in cycles of a neutron generator.

Referring now to FIG. 3, a schematic 300 illustrating an exemplary correspondence of bins to cycles of the pulsed neutron generator 102 is illustrated. As noted above, the synchronization signal emitted by the pulsed neutron generator 102 is indicative of time that a burst of neutrons is to be emitted from the pulsed neutron generator 102 (e.g., a time when the pulsed neutron generator 102 transitions from the "off" state to the "on" state). In the example shown in FIG. 3, bin 1 302 through bin M 304 correspond to time windows when the pulsed neutron generator is in the "on" state. For example, bin 1 302 can correspond to the first 5 µs after the pulsed neutron generator 102 transitions to the "on" state, a second bin may correspond to the next 5 µs (e.g., 5-9 ns), and so on. Bin M+1 306 can correspond to the first time window after the pulsed neutron generator 102 transitions from the "on" state to the "off" state, and bin M+N 308 can correspond to a last time window prior to the pulsed neutron generator 102 transitioning from the "off" state back to the "on" state. As noted above, the analyzer circuit 108 can assign pulses output by the detector 106 to respective bins based upon when the analyzer circuit 108 received the pulses relative to when the pulsed neutron generator 102 transitioned to the "on" state (e.g., based upon the synchronization signal).

Figure 4:
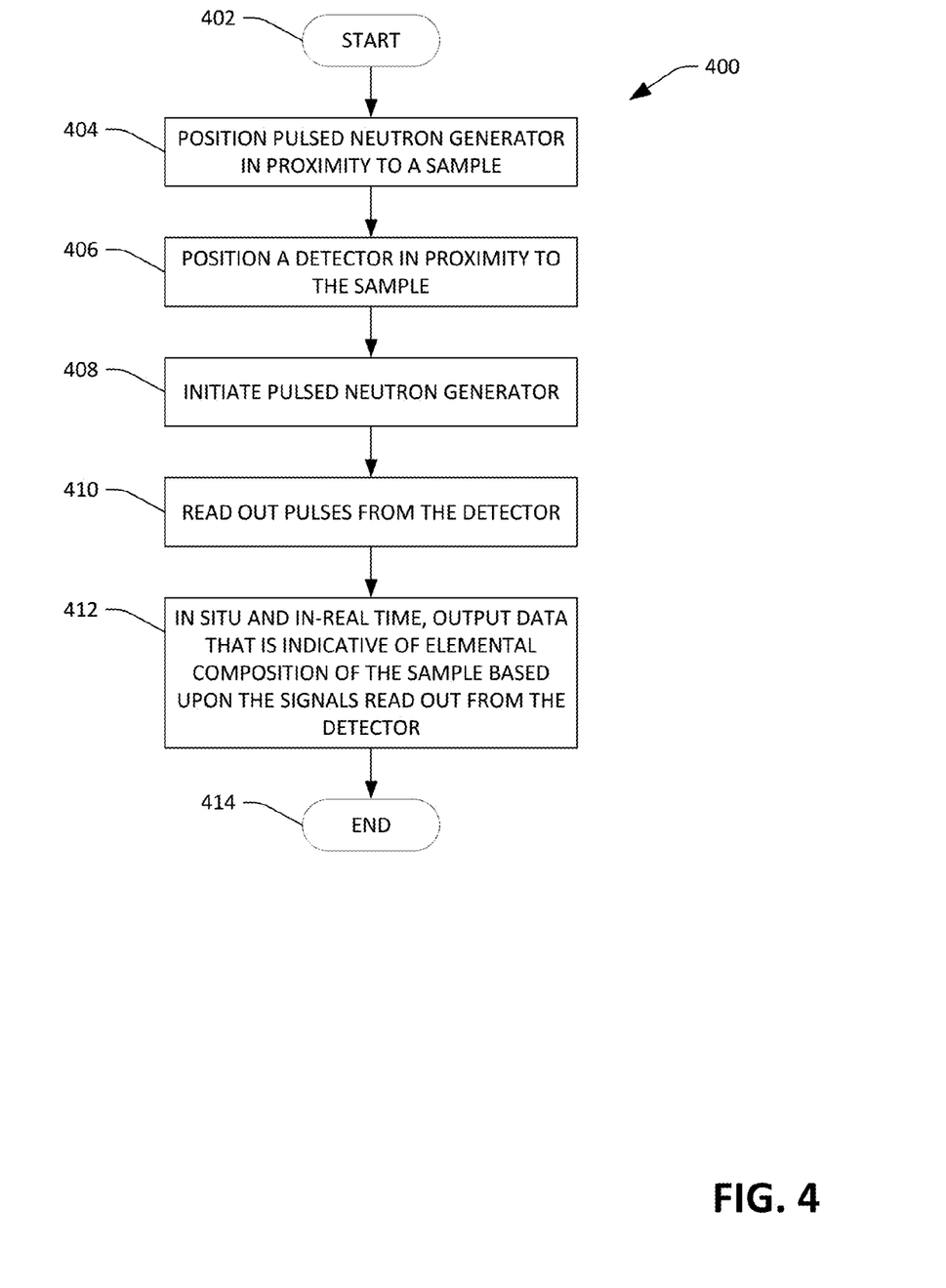
FIG. 4 is a flow diagram that illustrates an exemplary methodology for computing data that is indicative of elemental composition of a sample that comprises fissile material.

Now referring to FIG. 4, an exemplary methodology 400 for in situ and real-time generation of data that is indicative of elemental composition of a sample that comprises fissile material is illustrated. The methodology 400 starts at 402, and at 404, a pulsed neutron generator is positioned in proximity to a sample. For example, the pulsed neutron generator can be positioned within 0.5-4 feet of the sample, wherein the sample comprises fissile material. At 406, a detector is positioned in proximity to the sample, such that the sample is positioned in between the pulsed neutron generator and the detector. For example, the detector can be positioned at a distance of 0.5-4 feet of the sample. At 408, the pulsed neutron generator is initiated, such that the pulsed neutron generator begins to emit bursts of neutrons at a known rate and a known duty cycle. At 410, electric pulses are read out from the detector, wherein the pulses are indicative of energies of gamma rays that impact the detector. At 412, in situ and in real-time, data that is indicative of elemental composition of the sample is output based upon the pulses read out from the detector. As used herein, the term "real-time," in an example, refers to the ability to output data that is indicative of the elemental composition of the sample within two hundred micro-seconds of the pulsed neutron generator being initiated. In another example, the term "real-time" refers to the ability to output data that is indicative of the elemental composition of the sample within thirty seconds of the pulsed neutron generator being initiated. In yet another example, the term "real-time" refers to the ability to output data that is indicative of the elemental composition of the sample within thirty minutes of the pulsed neutron generator being initiated. The methodology 400 completes at 414.

Figure 5:
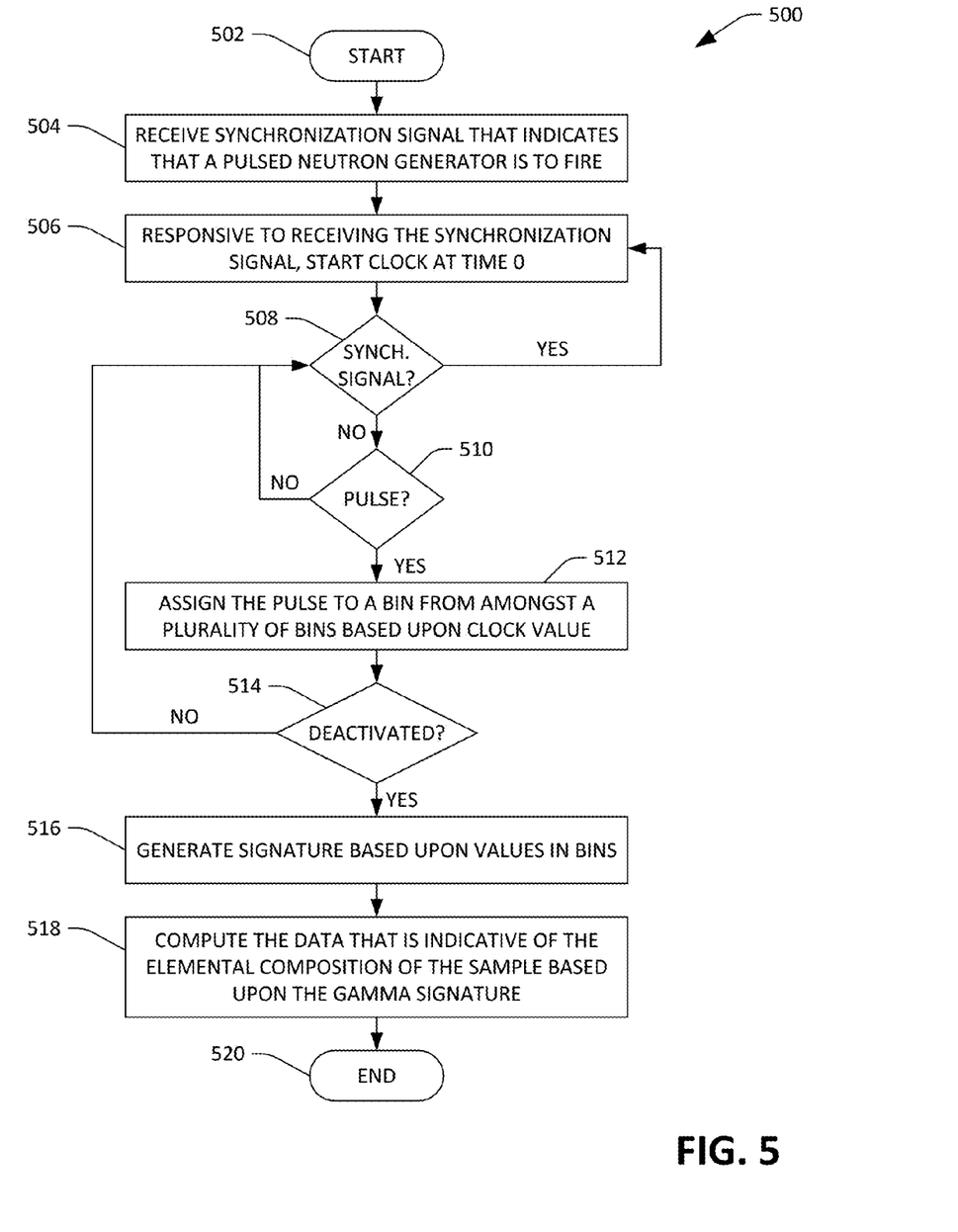
FIG. 5 is a flow diagram that illustrates an exemplary methodology for computing data that is indicative of elemental composition of a sample that comprises fissile material.

With reference now to FIG. 5, an exemplary methodology 500 for generating data that is indicative of elemental composition of a sample that comprises fissile elements is illustrated. For example, the methodology 500 refers to acts that occur during act 412 of the methodology 400. The methodology 500 starts at 502, and at 504, a synchronization signal is received that indicates commencement of a neutron burst emitted from the pulsed neutron generator 102. At 506, in response to receiving the synchronization signal, the clock 110 is initialized and started (at time zero). At 508, a determination is made regarding whether another synchronization signal has been received. If another synchronization signal has been received, the methodology 500 returns to 506, where the clock is re-initialized and started.

If at 508 no synchronization signal has been received, at 510 a determination is made regarding whether an electric pulse has been received from the detector 106. If no electric pulse has been received, the methodology 500 returns to 508. If at 510 it is determined that an electric signal has been received from the detector, then the methodology proceeds to 512, where the received pulse (the pulse amplitude) is assigned to a bin from amongst a plurality of bins based upon the value of the clock when the pulse is received. At 514, a determination is made regarding whether the pulsed neutron generator 102 has been deactivated. If the pulsed neutron generator has not been deactivated, the methodology returns to 508.

If at 514 it is determined that the pulsed neutron generator 102 has ceased operation, then at 516 a signature corresponding to pre-fission inelastic gamma rays is generated based upon the signals assigned to the bins. This signature can be generated, for example, by determining an equilibrium of delayed gamma rays through analysis of pulses in bins corresponding to later time windows in the "off" state of the pulsed neutron generator 102. At 518, data that is indicative of the elemental composition of the sample is computed based upon the signature. For example, the signature can be compared with a library of signatures of known elemental compositions and the data that is indicative of the elemental composition of the sample can be generated based upon such comparison. The methodology 500 completes at 520.

EXAMPLES

By way of example and not limitation, the following examples are illustrative of various embodiments of the present disclosure.

Example 1: Neutron Induced Gamma Ray Count Rate Profile

A prototype system was constructed, where the prototype included a commercial D-D neutron generator that was configured to pulse at 10 kHz and 25% duty cycle. Gamma rays were detected using an ORTEC HPGe detector whose output was connected to a XIA digital gamma ray spectrometer. The firmware was customized to obtain multiple time-resolved energy spectra by tagging each incoming pulse with its arrival time (relative to the gate signal of the neutron generator) and subsequently sorting the pulse amplitude into the appropriate member of a set of onboard energy spectra based on the value of the time tag. In the prototype, as many as 16 spectra were possible, and the 16 spectra were associated with up to eight time intervals during the "on" state of the neutron generated and up to eight more time intervals during the "off" state of the neutron generator.

Figure 6:
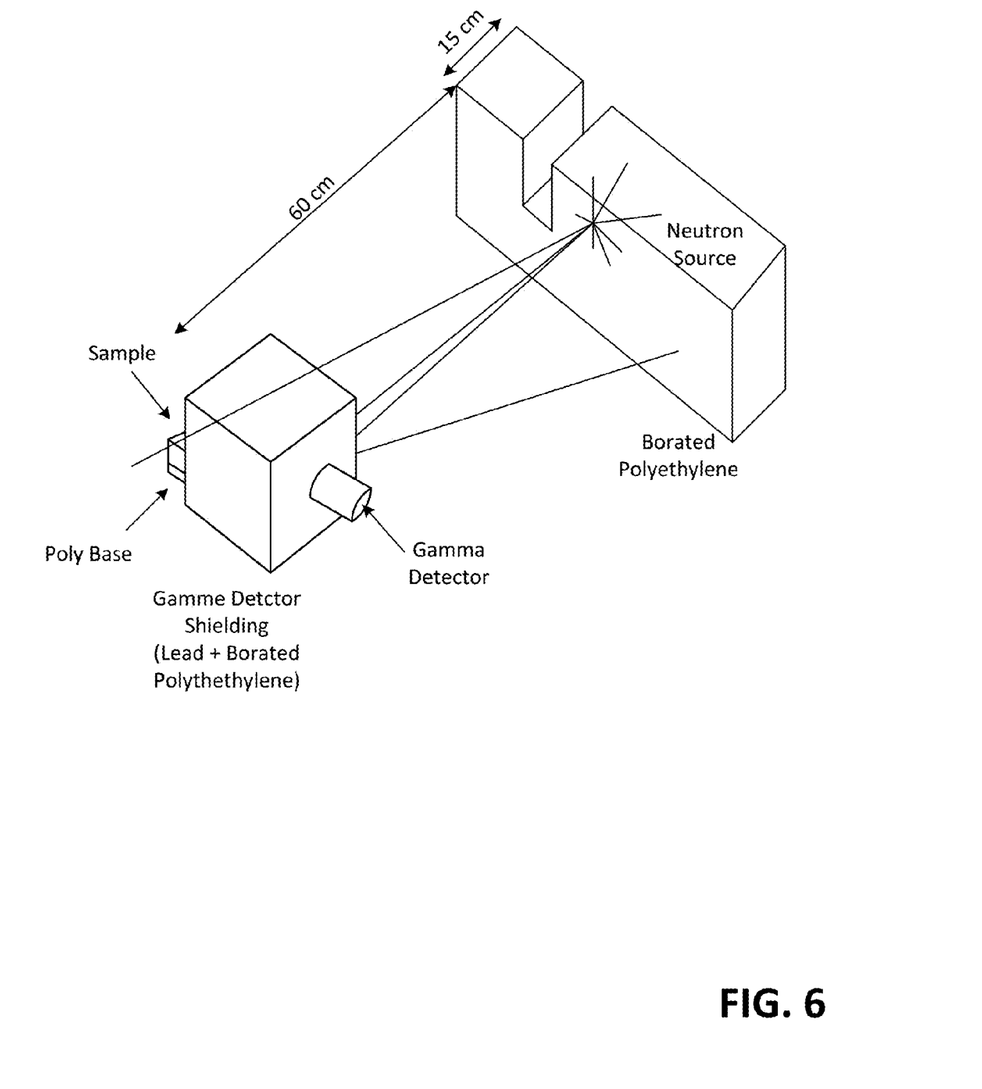
FIG. 6 illustrates an exemplary computation model geometry used in simulations.

Additionally, Monte Carlo simulations were performed on the interrogation experiments using MCNP6 based on the computational model geometry shown in FIG. 6. The detector was shielded by 6 cm thick lead, which surrounded the detector on all sides except for the side facing the sample. The outside shielding was 2.54 cm thick borated polyethylene that enclosed all sides of the detector. Borated polyethylene was also placed around the neutron generator to further reduce the neutron interactions with the detector.

Figure 7:
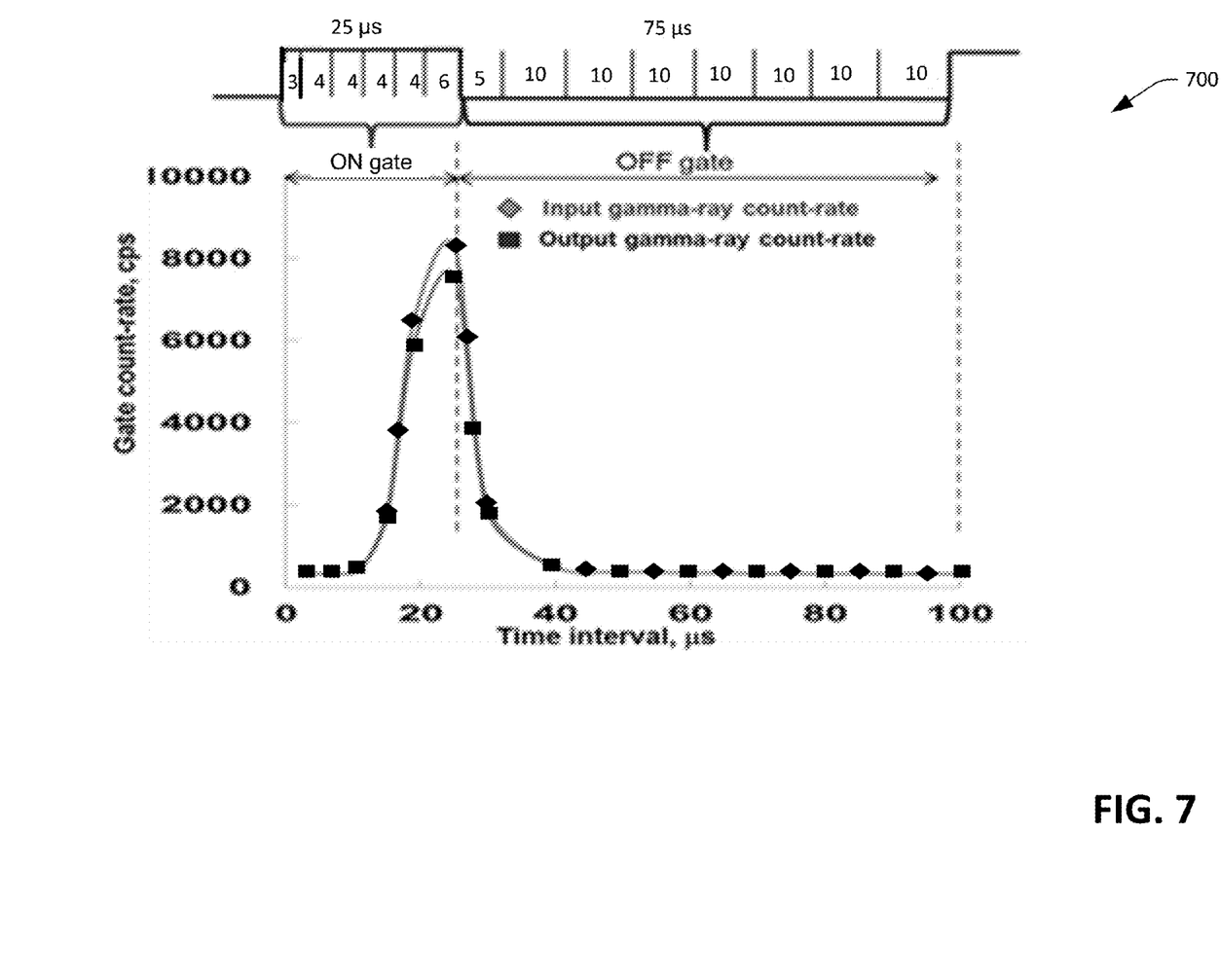
FIG. 7 illustrates input and output gamma ray count rates recorded during an experiment.

FIG. 7 is a chart 700 that shows the input gamma ray count rate (ICR) and output count rate (OCR) recorded for each of the time intervals during a one hour data acquisition run with a 10.2 cm cube of iron as a test sample. The results indicate that fast neutrons were produced only after about 10 µs from the beginning of the "on" gate when the pulsed neutron generator was turned on and were present at about 5 µs into the "off" gate after the neutron burst. Evidence of the fast neutron thermalization during the "off" gate was observed in the decrease of ICR and OCR at about 15 µs after the neutron burst with near equilibrium being reached to the end of the "off" gate. This is consistent with the TNC prompt gamma ray count rates of boron and hydrogen (constituents of the borated polyethylene shielding material), which also attained an equilibrium value in each of the 10 µs sub-interval set within the neutron generator "off" gate. The equilibrium condition for the thermal neutron flux within the "off" gate has implications for the online measurement of very short-lived fission products. These signals are easily measured as opposed to the conventional technique where the sample needs to be cycled between an irradiation location and a counting station. In addition, the ICR and OCR versus neutron pulse timing curve can also be used to determine the optimal setting of the "on" and "off" gates so that the INS and TNC prompt gamma ray spectra would be free from mutual interferences.

Figure 8:
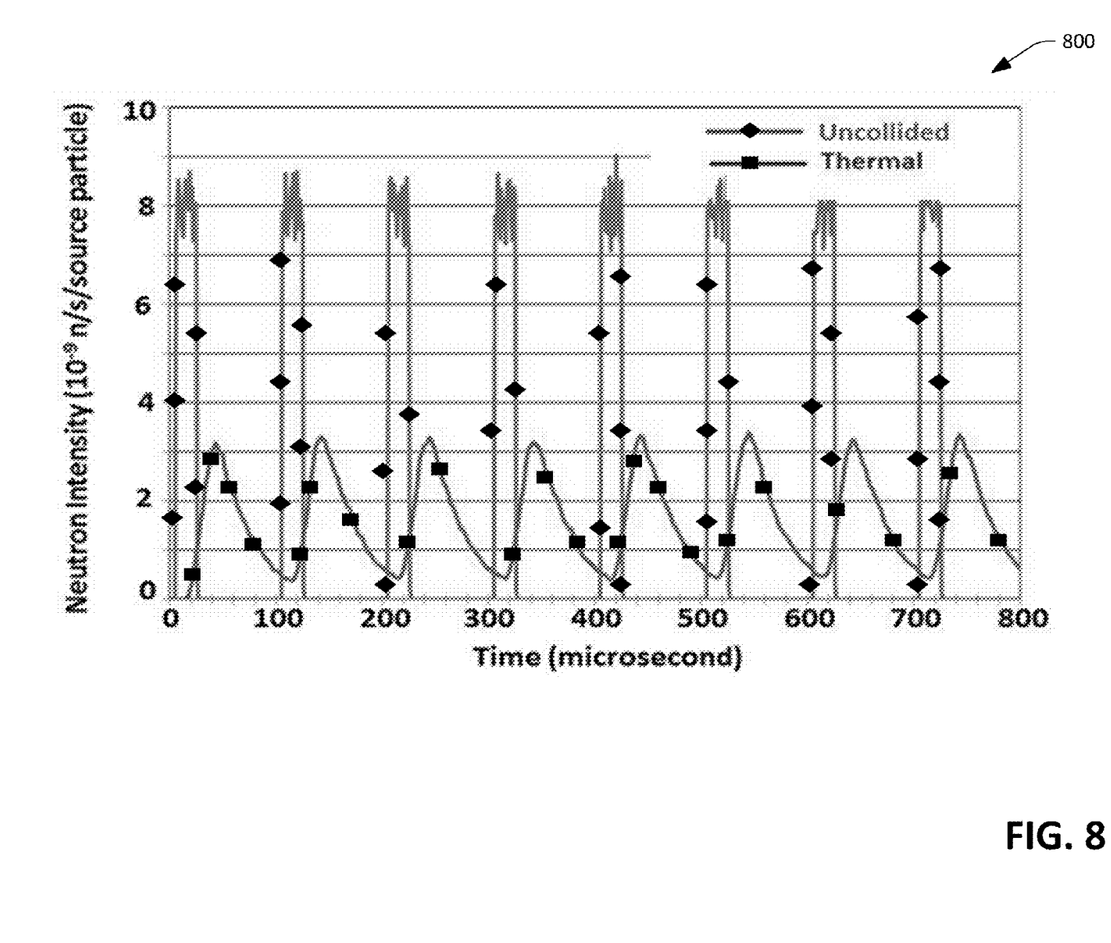
FIG. 8 illustrates a plot corresponding to a simulation of a temporal profile of D-D neutrons pulsed at a repetition rate of 10 kHz and 25% duty cycle.

The MCNP6 simulation results for the un-collided source neutron and thermal neutron profiles are shown in a chart 800 in FIG. 8 for a neutron generator with 10 kHz repetition rate and 25% duty cycle. It was found that the experimentally-observed equilibrium condition did not appear in the MCNP6 simulations of the multi-gate system.

Example 2: Active Interrogation of Depleted Uranium Samples

A large Plexiglass box containing small samples of depleted uranium was interrogated using the pulsed D-D neutron generator. The most prominent measured prompt gamma rays, produced by INS reactions, are summarized in Table 1, along with the signal-to-noise ratio for each line. The noise was calculated assuming that the gamma ray count rate followed Poisson statistics. These results were obtained for a gate width of 4 µs set during a burst. The corresponding gate runtime was 145 seconds for a total runtime of one hour. The thermal neutron absorption cross-section for $^{238}$U is negligible, and accordingly, only the lines from natural decay were observed between the neutron bursts.

| Energy (keV) | Signal-to-Noise |
|---|---|
| 680 | 1.4 |
| 885 | 3.2 |
| 1015 | 1.9 |

Detection of the characteristic INS gamma rays is a much improved approach to the identification of fissile material (even when present as mixtures) compared to current techniques, where the material was interrogated with neutrons or photons and the relative intensities of the β-delayed gamma ray line pairs of fission products are measured to quantify the material.

Figure 9:
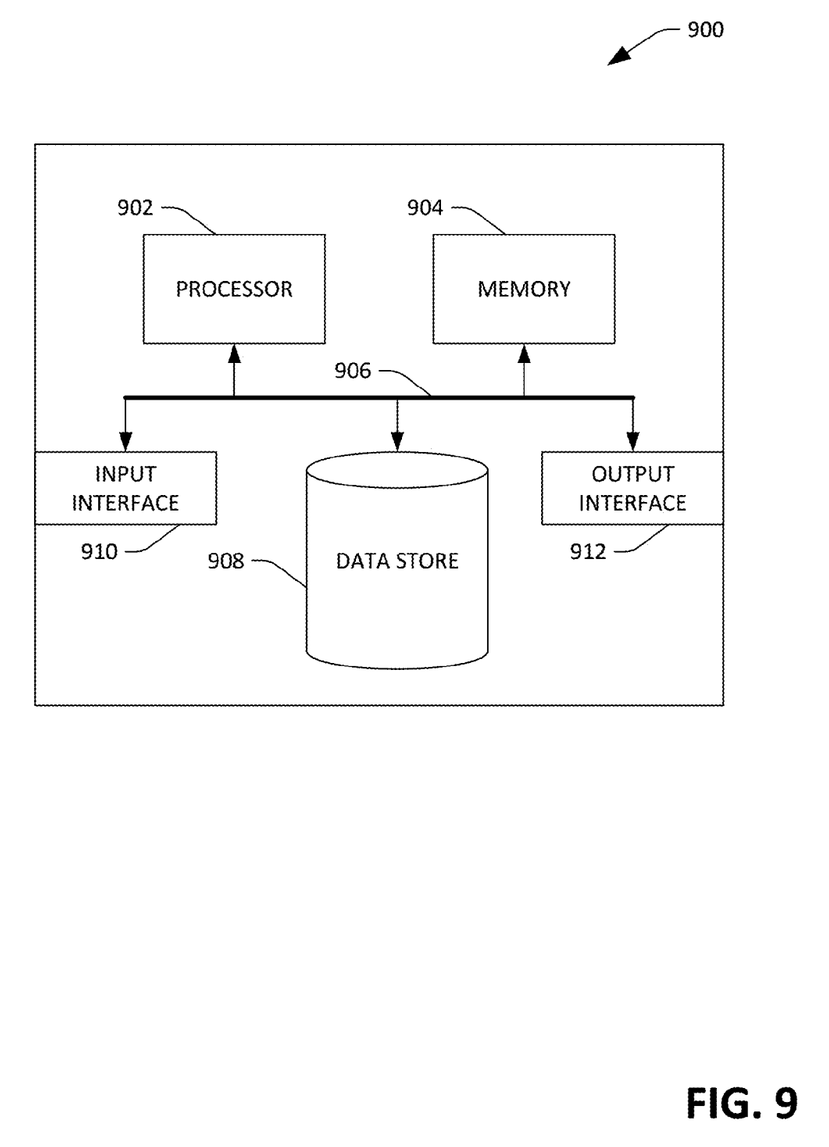
FIG. 9 illustrates an exemplary computing system.

Referring now to FIG. 9, a high-level illustration of an exemplary computing device 900 that can be used in accordance with the systems and methodologies disclosed herein is illustrated. For instance, the computing device 900 may be used in a system that is configured to generate data that is indicative of elemental composition of a sample. The computing device 900 includes at least one processor 902 that executes instructions that are stored in memory 904. The instructions may be, for instance, instructions for implementing functionality described as being carried out by one or more components discussed above or instructions for implementing one or more of the methods described above. The processor 902 may access the memory 904 by way of a system bus 906. In addition to storing executable instructions, the memory 904 may also store images, depth data, etc.

The computing device 900 additionally includes a data store 908 that is accessible by the processor 902 by way of the system bus 906. The data store 1208 may include executable instructions, characteristic energy spectra, pulse amplitudes, etc. The computing device 900 also includes an input interface 910 that allows external devices to communicate with the computing device 900. For instance, the input interface 910 may be used to receive instructions from an external computer device, from a user, etc. The computing device 900 also includes an output interface 912 that interfaces the computing device 900 with one or more external devices. For example, the computing device 900 may display text, images, etc. by way of the output interface 912.

It is contemplated that the external devices that communicate with the computing device 900 via the input interface 910 and the output interface 912 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 900 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 900 may be a distributed system. Thus, for instance, several devices may be in communication by way of a network connection and may collectively perform tasks described as being performed by the computing device 900.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

As used herein, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference, and the term "about" refers to a range of 10% of the value to which the term applies.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A system comprising:
   a pulsed neutron generator that is configured to emit a burst of neutrons;
   a detector that is configured to output a plurality of pulses based upon a plurality of gamma that rays that impinge upon the detector, the gamma rays emitted from a sample that comprises fissile material in response to an emitted neutron in the burst of neutrons initiating a nuclear reaction in the sample, each pulse has a respective amplitude;
   an analyzer circuit that is configured to assign each pulse to a respective temporally-based bin from amongst a plurality of temporally-based bins, the selected based upon a difference in time between:
     when the pulse was received at the analyzer circuit; and
     when the pulsed neutron generator commenced emitting the burst of neutrons; and
   a computing device that is configured to identify an equilibrium of delayed gamma rays based upon the bins to which the pulses are assigned and the amplitudes of the pulses, and further configured to generate data that is indicative of elemental composition of the sample based upon the identified equilibrium and the pulses, the computing device is configured to generate the data in situ.

2. The system of claim 1, the pulsed neutron generator being a deuterium-deuterium neutron generator.

3. The system of claim 1, the pulsed neutron generator being a deuterium-tritium neutron generator.

4. The system of claim 1, the pulsed neutron generator configured to emit bursts of neutrons at a rate of about 10 kHz.

5. The system of claim 4, the pulsed neutron generator has a duty cycle of about 25%.

6. The system of claim 1, the pulsed neutron generator is in communication with the analyzer circuit, the pulsed neutron generator is configured to emit a synchronization signal to the analyzer circuit that is indicative of commencement of the burst of neutrons, the analyzer circuit assigns each of the pulses to its respective bin based upon the synchronization signal received from the pulsed neutron generator.

7. The system of claim 6, the analyzer circuit comprises a clock that is initialized and started responsive to the analyzer component receiving the synchronization signal from the pulsed neutron generator, the analyzer circuit assigns each of the pulses to its respective bin based upon a value of the clock when the analyzer circuit receives the pulse.

8. The system of claim 1, the pulsed neutron generator emits the burst of neutrons as a portion of a cycle, the cycle comprises a first time window when the neutron generator is emitting the burst of neutrons and a second time window when the neutron generator fails to emit neutrons, the first time window corresponds to a first subset of bins in the plurality of bins, the second time window corresponds to a second subset of bins in the plurality of bins.

9. The system of claim 8, a number of bins in the first subset of bins is equivalent to a number of bins in the second subset of bins.

10. The system of claim 1, the plurality of bins respectively correspond to a plurality of time windows, wherein a first length of a first time window in the plurality of time windows is different from a second length of a second time window in the plurality of time windows.

11. The system of claim 1, the plurality of bins respectively correspond to a plurality of time windows, wherein a time window corresponding to the bin is between five microseconds and fifteen microseconds in length.

12. A method comprising:
   initiating a pulsed neutron generator, the pulsed neutron generator periodically emits bursts of neutrons;
   reading out a plurality of pulses from a detector, the pulses generated by the detector based upon gamma rays upon the detector, the gamma rays emitted from a sample that comprises fissile material in response to an emitted neutron in a burst of neutrons emitted by the pulsed neutron generator initiating a nuclear reaction in the sample;
   identifying an equilibrium level of delayed gamma rays emitted from the sample based upon the plurality of pulses; and
   in situ and in real-time, outputting data that is indicative of elemental composition of the sample based upon the pulses read out from the detector and the identified equilibrium level of delayed gamma rays.

13. The method of claim 12, further comprising generating the data that is indicative of the elemental composition of the sample based upon the pulses read out from the detector and the identified equilibrium level of delayed gamma rays, wherein generating the data comprises:

assigning the pulse to a bin from amongst a plurality of possible bins based upon an amount of time between:
a time of commencement of the burst of neutrons emitted by the pulsed neutron generator; and
a time when the signal is read out from the detector; and
generating the data based upon an amplitude of the pulse and a bin to which the signal is assigned.

14. The method of claim 13, wherein generating the data that is indicative of the elemental composition of the sample comprises:

synchronizing the pulsed neutron generator with a circuit that assigns each of the pulses to its respective bin from amongst the plurality of bins, the circuit assigns the pulses to their respective bins based upon the pulsed neutron generator being synchronized with the circuit.

15. The method of claim 14, wherein synchronizing the pulsed neutron generator with the circuit comprises initializing and starting a clock of the circuit responsive to the circuit receiving a synchronization signal output by the pulsed neutron generator.

16. The method of claim 12, wherein generating the data that is indicative of the elemental composition of the sample comprises:

extracting a signature for the sample based upon pulses assigned to the plurality of bins;
comparing the signature with a library of known signatures; and
generating the data that is indicative of the elemental composition of the sample based upon the comparing of the signature with the library of known signatures.

17. The method of claim 12, the pulsed neutron generator is a deuterium-deuterium pulsed neutron generator.

18. The method of claim 12, further comprising defining a number of bins in the plurality of bins based upon user input.

19. The method of claim 12, further comprising defining time windows that respectively correspond to the plurality of bins based upon user input.

20. A system comprising:

a pulsed neutron generator that periodically emits bursts of neutrons;
a detector that outputs pulses based upon gamma rays impinging upon material of the detector, the pulses have respective amplitudes, the gamma rays emitted from a sample in response to the sample being actively interrogated by the neutrons in the bursts of neutrons, the sample comprises fissile material;
an analyzer circuit that assigns each pulse to a respective temporally-based bin from amongst a plurality of temporally-based bins based upon when the pulse was received at the analyzer circuit; and
a computing device that identifies an equilibrium level of delayed gamma rays emitted from the sample based upon the bins to which the pulses were respectively assigned and the amplitudes of the pulses, and that generates and outputs, in situ and in real-time, data that is indicative of elemental composition of the sample based upon the identified equilibrium level of delayed gamma rays and the pulses.

* * * * *